United States Patent [19]

Schulze

[11] 4,066,649

[45] Jan. 3, 1978

[54] METHOD OF PRODUCING N,N'-(DIMETHYL) PIPERAZINE COMPOUNDS

[75] Inventor: Heinz Schulze, Austin, Tex.

[73] Assignee: Texaco Development Corporation, New York, N.Y.

[21] Appl. No.: 642,225

[22] Filed: Dec. 19, 1975

[51] Int. Cl.² .................. C07D 295/02; C07D 241/38
[52] U.S. Cl. ............................................. 260/268 SY
[58] Field of Search ................................. 260/268 SY

[56] References Cited

U.S. PATENT DOCUMENTS

| | | | |
|---|---|---|---|
| 2,467,205 | 4/1949 | Gresham et al. | 260/268 SY |
| 2,839,533 | 6/1958 | Scigliano et al. | 260/268 SY |
| 3,112,317 | 11/1963 | Marschall et al. | 260/268 SY |
| 3,324,130 | 6/1967 | Ham et al. | 260/268 SY |
| 3,342,820 | 9/1967 | Brader | 260/268 SY |
| 3,383,417 | 5/1968 | Lichtenwaltey | 260/268 SY |
| 3,429,909 | 2/1969 | Schuster | 260/268 SY |
| 3,647,795 | 7/1972 | Bluestein et al. | 260/268 SY |
| 3,766,184 | 10/1973 | Johansson et al. | 260/268 SY |

*Primary Examiner*—Paul M. Coughlan, Jr.
*Assistant Examiner*—Jose Tovar
*Attorney, Agent, or Firm*—Carl G. Ries; Thomas H. Whaley; James L. Bailey

[57] ABSTRACT

An improved process for producing N,N'-(dimethyl) piperazine compounds is disclosed wherein monoethanolamine or a C-lower alkyl substituted primary 1-amino-2-alkanol is contacted with methyl alcohol in the presence of a catalytically effective amount of a phosphorous-containing substance at a temperature of about 150° C. to about 350° C. under a pressure sufficient to maintain the mixture essentially in liquid phase, said N,N'-(dimethyl) piperazine compounds produced having the formula:

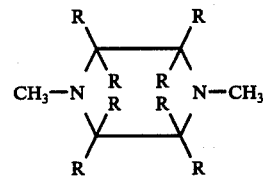

wherein each R is independently hydrogen or a lower alkyl radical, and, recovering from the resultant reaction mixture said N,N'-(dimethyl) piperazine.

8 Claims, No Drawings

METHOD OF PRODUCING N,N'-(DIMETHYL) PIPERAZINE COMPOUNDS

BACKGROUND OF THE INVENTION

1. Field of the Invention

This invention relates to a process for the preparation of N,N'-(dimethyl) piperazine compounds such as N,N'-(dimethyl) piperazine and more particularly, pertains to an improved liquid phase catalyzed process for preparing N,N'-(dimethyl) piperazine compounds.

2. Description of the Prior Art

Piperazine compounds and N,N'-(disubstituted) piperazine compounds are well known, having established utility in a myriad of applications in the chemical as well as the food-related arts.

Many methods of producing piperazine are well known. In one method for piperazine synthesis, diethanolamine and ammonia are reacted at relatively high temperatures and high pressures, e.g., 1,700 to 1,850 psig, see, for example, U.S. Pat. No. 2,910,477. It has also been disclosed that N,N'-bis-(2-hydroxyethyl) piperazine can be produced by heating diethanolamine in the presence of a molar excess of a carboxylic acid containing eight or more carbon atoms. See, for example, German Pat. No. 1,002,359.

Additionally, it has been disclosed that N,N'-bis-(2-hydroxyethyl) piperazine can be produced by bimolecular dehydration of diethanolamine with certain inorganic acid catalysts and particularly phosphoric acid and acid salts. See, for example, U.S. Pat. No. 2,636,033.

Unexpectedly, it has been found that N,N'-(dimethyl)-piperazine compounds, including the N,N-(dimethyl) C-(alkyl) substituted) piperazines, can be produced from the readily available and easily obtainable corresponding monoethanolamine or C-lower alkyl substituted monoethanolamines and methyl alcohol. One outstanding feature of the instant invention resides in the simplicity and availability of the reactants. Another outstanding facet of the instant invention is the fact that the desired compound is achieved in a single process step whereas such desired N,N'-(dimethyl) piperazine compounds are usually produced via multi-step and complicated processes.

SUMMARY OF THE INVENTION

In accordance with the broad aspects of the instant invention, N,N'-(dimethyl) piperazine compounds of the formula:

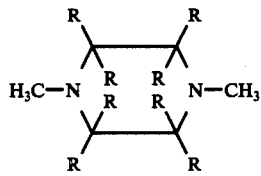

wherein each R is independently hydrogen or a lower alkyl radical are produced by a process which includes contacting a primary amine comprising monoethanolamine or a C-lower alkyl substituted monoethanolamine with methyl alcohol in the presence of a catalytically effective amount of a phosphorous-containing substance at a temperature of from about 150° C. to about 350° C. under pressure sufficient to maintain the mixture essentially in liquid phase; and recovering from the resultant reaction mixture the N,N'-(dimethyl) piperazine compound.

DESCRIPTION OF THE PREFERRED EMBODIMENTS

In accordance with this invention, a process for producing an N,N'-(dimethyl) piperazine compound is provided. In brief, the preferred process comprises the steps of reacting a methyl alcohol with monoethanolamine or a C-lower alkyl monoethanolamine in the presence of a catalytically effective amount of a phosphorous-containing substance from about 150° C. to about 350° C. under pressure sufficient to maintain the resultant reaction mixture essentially in liquid phase.

The N,N'-(disubstituted) piperazine compounds that can be produced in accordance with the instant invention can be depicted by the formula:

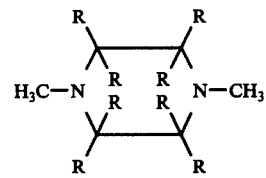

wherein each R is independently hydrogen or a lower alkyl radical. Examples of these compounds depending upon the primary alcohol and monoethanolamine reactant employed include N,N'-dimethylpiperazine, N,N'dimethyl-3,5-diethylpiperazine and the like.

The amine reactant which is reacted with methanol may be depicted as having the formula:

Thus, depending upon the particular monoethanolamine used, R in the above formula may be hydrogen or any lower alkyl substituted radical, preferably those lower alkyl radicals containing one to four carbon atoms. These include methyl, ethyl, N-propyl, isopropyl, t-butyl, isobutyl, n-butyl, etc. radicals.

Suitable phosphorous-containing substances which can be employed as catalysts include, for example, acidic metal phosphates, phosphoric acid compounds and their anhydrides, phosphorous acid compounds and anhydrides, alkyl or aryl phosphate ester, alkyl or aryl phosphite esters, alkyl or aryl substituted phosphorous and phosphoric acids, alkali metal monosalts of phosphoric acid, the thioanalogs of the foregoing, and mixtures of any of the above.

More particularly, suitable acidic metal phosphates include boron phosphate, ferric phosphate, aluminum phosphate, etc.

Suitable phosphoric acid compounds include aqueous orthophosphoric acidsphoric acid, metaphosphoric acid, and condensed phosphoric acids such as polyphosphoric acids. Accordingly, an example of a suitable phosphorous acid is orthophorphorous acid.

In addition, any commerically available mono-, di-, or tri-alkyl or aryl phosphate or phosphite ester can be employed as the catalyst in the inventive process. Additionally, bis(phosphates) and secondary phosphate esters such as those disclosed in U.S. Pat. No. 3,869,526 and U.S. Pat No. 3,869,527, respectively, can be used.

Preferably, the lower alkyl esters are employed such as those having from one to about eight carbon atoms per alkyl group. Preferred aryl esters contain from about six to 20 carbon atoms and may include a phenyl group or alkyl-substituted phenyl group.

Further, suitable alkyl or aryl substituted phosphorous and phosphoric acids which may be employed as a catalyst include alkyl phosphinic acids, aryl phosphonic acids, alkyl phosphinic acids and aryl phosphinic acids. Preferably, such acids include alkyl or aryl groups and have from one to about 20 carbon atoms in each aryl or alkyl group.

Specific examples of alkyl or aryl substituted phosphorous and phosphoric acids that may be used in accordance with the invention are phenylphosphinic acid, ethylphosphonic acid, phenylphosphonic acid, naphthaphosphonic acid, and methylphosphinic acid. Examples of the alkyl aryl substituted phosphorous and phosphoric acid esters are methylphenyl phosphonate, dimethylphenyl phosphonate, methylphenyl phosphinate, ethyl naphthaphosphinate, and propylmethyl phosphonate.

The above-mentioned phosphorous-containing substances are not intended to be exhaustive of those that can be employed as a catalyst in the inventive process. Those materials set forth are merely intended to be representative of the types of substances that we have found to be particularly effective. Yet, of the substances and the types of compounds mentioned, we particularly prefer to employ those that are known to be most reactive such as orthophosphoric acids, polyphosphoric acids, boron phosphate, aluminum phosphate, ferric phosphate, and orthophosphorous acid. Of these, most preferred is orthophosphorous acid.

The phosphorous-containing substance is employed in only a catalytically effective amount, normally from about 0.1 to about 10.0 mole percent, more often 1.0 to 5.0 mole percent based on the monoethanolamine or C-lower alkyl substituted monoethanolamine employed as a reactant. Most often the amount of catalyst used is 1.0 to 3.0 mole percent. Preferably, the phosphorous-containing substance is not employed in an amount higher than about 5.0 mole percent, based upon the amine reactant present, inasmuch as phosphorylation reactants can occur if higher amounts are used which adversely affect the yield of desirable products. The particular amount employed for a given reaction can vary widely, however, depending upon the reactivity of the catalyst material, reactivity of reactants, types of reactants employed and particular processing conditions employed.

The specific phosphorous-containing substance employed as a catalyst can be employed alone, in combination with other phosphorous-containing substances or can be used in combination with other acid materials. For example, it has been found that phosphoric acid-impregnated silicas or admixtures of orthophorphorous acid and silica-alumina can be utilized. Other materials that may be used with the phosphorous-containing substance include alpha- and gamma-aluminas, silica, carborundum, etc. When an additional catalyst is used it is present in an amount of 0.1 to 10.0 weight percentage additional catalyst based upon the amine employed.

The reactants and the catalyst, all described hereinabove, are admixed in any desired manner so as to provide intimate admixture of reactants and intimate contact thereof with the catalyst. The admixture is then heated to a temperature of from about 150° C. to about 350° C., preferably from 200° C., under a pressure sufficient to maintain the reaction mass in liquid phase which normally ranges from about atmospheric (14 psig) to about 3,000 psig, depending upon reactants employed. More often the pressure range is atmospheric to 2,000 psig, and most often is 500–2,000 psig. The reaction is allowed to proceed at the temperature employed until the desired amount of conversion is obtained.

Time of reaction has not been found to be critical and complete conversion can usually be determined by the cessation of formation of water of reaction. It is also not critical to control the amount of water of reaction present during the reaction, such as by removal thereof as it is formed. Usually, we prefer to carry out the reaction as the above-described temperatures for about ½ to about five hours.

Normally, the monoethanolamine or substituted amine compound and the methyl alcohol are reacted at molar ratios of from about 1:1 to about 1:2, preferably about 1:1 to about 1:1.5, moles amine per mole of methyl alcohol.

The process of the invention can be carried out batchwise or continuously employing well known batch and continuous processing techniques and conventional processing apparatus. Where the process is carried out continuously, we prefer to employ space velocities of reactants of from about 0.1 to about 4.0, and preferably from about 0.5 to 2.0, grams total reactants per milliliter of total reactor volume per hours.

The desired N,N'-(dimethyl) piperazine compound can be readily recovered from the reaction product mass in substantially pure form by conventional procedures, such as by distillation without difficulty. For example, the reaction product mass may be directly distilled, or initially filtered to remove formed solids which usually are amine salt complexes of the phosphorous-containing substance, and then distilled. The desired N,N'-(dimethyl) piperazine compound can then be separately collected overhead in salt-free form. Such distillation recovery procedures are well known in the art, and, therefore, will not be more particularly discussed herein.

EXAMPLE I

A mixture of monoethanolamine (305 g 5.0 mol), methanol (192 g 6.0 mol) and 85 percent phosphoric acid (11.4 g 0.1 mol) was heated three hours at 300° C. in a 1 l stirred autoclave. Maximum pressure was 1,600 psi. The reaction product was filtered with Supercell filter aid (5 g) and the filtrate (446 g) distilled through a 50 cm. packed column until the pot temperature reached 250° C. Stillhead temperatures did not exceed 100° C. The yield of distillate was 301 g. GLC (area percent) indicated 25 percent dimethylpiperazine and 63.3 percent water. Karl Fisher analysis indicated 51.5 percent $H_2O$. Total amine titration indicated two breaks at 4.01 and 7.17 meg/g. The residue (87.5 g and 15 g solids) consisted of phosphate salts and ethylene piperazine type polymers which were not identified.

While the invention has been explained in relation to its preferred embodiments, it is understood that various modifications thereof will become apparent to those skilled in the art upon reading the specification and is intended to cover such modifications as fall within the scope of the appended claims.

I claim:

1. An improved process for producing an N,N'-(dimethyl) piperazine compound of the formula:

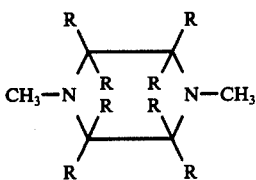

wherein each R is, independently, hydrogen or a $C_{1-4}$ lower alkyl radical comprising the step of:

contacting a monoethanol amine having the formula:

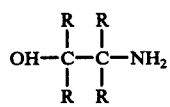

wherein each R, independently, is hydrogen or a $C_{1-4}$ lower alkyl radical with methyl alcohol in the presence of a catalytically effective amount of a phosphorus-containing substance selected from the group consisting of acidic metal phosphates, orthophosphoric acid, metaphosphoric acid, polyphosphoric acid, orthophosphorous acid, alkyl or aryl phosphate esters, alkyl or aryl phosphite esters, alkyl or aryl substituted phosphorus and phosphoric acids wherein said alkyl groups have from 1 to 8 carbon atoms and said aryl groups have from 6 to 20 carbon atoms, alkali metal monosalts of phosphoric acid and mixtures of the above at a temperature of from 150° C to about 350° C. under pressure sufficient to maintain the mixture essentially in liquid phase; and recovering from the resultant reaction mixture said N,N'-(dimethyl) piperazine compound.

2. The process in accordance with claim 1 wherein said contacting is accomplished at a temperature from about 150° C. to about 350° C.

3. The process in accordance with claim 1 wherein said contacting is accomplished at a pressure ranging from about ambient to about 3,000 psig.

4. The process of claim 3 wherein said pressure ranges from about 500 to about 2,000 psig.

5. The process of claim 1 wherein the mole ratio of said monoethanolamine to said methyl alcohol reactant ranges from about 1:1 to about 1:2.

6. The process in accordance with claim 1 wherein said phosphorous-containing substance is present in an amount of about 0.1 to about 5.0 mole percent based upon the amount of said monoethanolamine present.

7. The process in accordance with claim 1 wherein said amine is monoethanolamine.

8. The process in accordance with claim 5 wherein said mole ratio is 1:1 to 1:1.5.

* * * * *